(12) United States Patent  
Humberstone

(10) Patent No.: US 9,377,442 B2  
(45) Date of Patent: Jun. 28, 2016

(54) PEST INSPECTION TOOL

(71) Applicant: Trade Management Systems Pty Ltd, Queensland (AU)

(72) Inventor: Michael Humberstone, Queensland (AU)

(73) Assignee: Trade Management Systems Pty Ltd., Queensland (AU)

( * ) Notice: Subject to any disclaimer, the term of this patent is extended or adjusted under 35 U.S.C. 154(b) by 263 days.

(21) Appl. No.: 14/246,805

(22) Filed: Apr. 7, 2014

(65) Prior Publication Data

US 2014/0318214 A1 Oct. 30, 2014

(30) Foreign Application Priority Data

Apr. 30, 2013 (AU) ................................. 2013901502

(51) Int. Cl.
  *G01N 29/04* (2006.01)
  *G01N 29/265* (2006.01)

(52) U.S. Cl.
  CPC ............ *G01N 29/045* (2013.01); *G01N 29/265* (2013.01)

(58) Field of Classification Search
  CPC ..... G01N 29/045; G01N 29/04; G01N 29/265; A01M 3/00; E04B 1/72
  USPC ........................................................ 73/12.09
  See application file for complete search history.

(56) References Cited

U.S. PATENT DOCUMENTS

| | | | | |
|---|---|---|---|---|
| 4,580,784 A | * | 4/1986 | Brill ........................ | A63B 47/02 294/19.2 |
| 6,561,918 B2 | * | 5/2003 | Kim ..................... | A63B 69/3685 473/242 |
| 7,862,408 B1 | * | 1/2011 | Weinstein .............. | A22C 9/007 452/102 |

* cited by examiner

*Primary Examiner* — Hezron E Williams  
*Assistant Examiner* — David Z Huang  
(74) *Attorney, Agent, or Firm* — Fish & Tsang LLP

(57) ABSTRACT

A tool for inspecting timber of a structure for the presence of damage to exposed timber caused by a pest. The tool includes a head having a substantially flat rear portion, and a generally concave front portion that forms an edge configured to permit the head to penetrate into a surface deviation in the timber, or into a boundary between the timber and a floor covering over a substantial portion of the height of the floor covering.

15 Claims, 5 Drawing Sheets

PEST INSPECTION TOOL

This application claims priority to Australian Patent Application Serial No. 2013901502 filed on Apr. 30, 2013. This and all other referenced extrinsic materials are incorporated herein by reference in their entirety.

The present invention relates to improvements in a tool designed to detect the presence of damage to timber caused by pests such as termites, borers, wood decay and ants.

BACKGROUND

The following description includes information that may be useful in understanding the present invention. It is not an admission that any of the information provided herein is prior art or relevant to the presently claimed invention, or that any publication specifically or implicitly referenced is prior art.

Tools exist for tapping internal and external timber structures and decorative timbers in a building and determining, by sound and/or tactile feel, whether pest activity has caused a deterioration in the timber. The damage caused by the pests is often centered around the area near the intersection of the baseboard and the floor and in the concave profile of moldings present in many decorative timbers. These areas are difficult to analyze. Conventional tools are not optimally configured for use with detecting the presence of timber damage due to tool-to-timber contact being minimal (for example, a round ball contacting the timber is has only a very small area of surface contact) and, due to the shape of standard tools, areas that a standard tool can test such as around the area near the intersection of the baseboard and the floor and in the concave profile of moldings present in many decorative timbers is limited. Therefore there exists a need for a tool configured to have a greater area of tool-to-timber contact to enhance the detection of damage to timber.

SUMMARY OF THE INVENTION

The present invention in one preferred aspect provides for a tool for inspecting timber in a structure for the presence of damage to timber caused by a pest. The tool includes a shaft having a proximal end, a distal end and a central longitudinal axis through the proximal and distal ends, the proximal end being configured to be gripped by a user. The tool further includes a head at the distal end, the head including a top portion for engagement with the distal end of the shaft and a bottom portion opposite the top portion, the top and bottom portions intersecting the central longitudinal axis of the shaft when the head is engaged thereto. The head includes a rear portion and a front portion opposite the rear portion, the rear and front portions each extending from the top portion to the bottom portion, the rear portion being substantially flat along a rear plane parallel to the central longitudinal axis of the shaft. The head includes opposed sides, the opposed sides each extending from the rear portion to the front portion, the opposed sides each extending from the top portion to the bottom portion, at least one of the sides having a concave portion that is concave in a plane perpendicular to the rear plane and perpendicular to the central longitudinal axis of the shaft when the head is engaged with the shaft, the concave portion of the at least one of the sides forming an edge with the rear portion. The edge is configured to permit the head to penetrate into a surface deviation in the timber, or into a boundary between the timber and a floor covering over a substantial portion of the height of the floor covering.

It is to be understood that both the foregoing general description and the following detailed description are exemplary and explanatory only and are not restrictive of the invention, as claimed. It will be understood that the term "comprising" is intended to have a broad, opening meaning and not limited to a particular embodiment.

The accompanying drawings, which are incorporated in and constitute a part of this specification, illustrate several embodiments of the invention and together with the description, serve to explain the principles of the invention.

DETAILED DESCRIPTION

Figure 1:
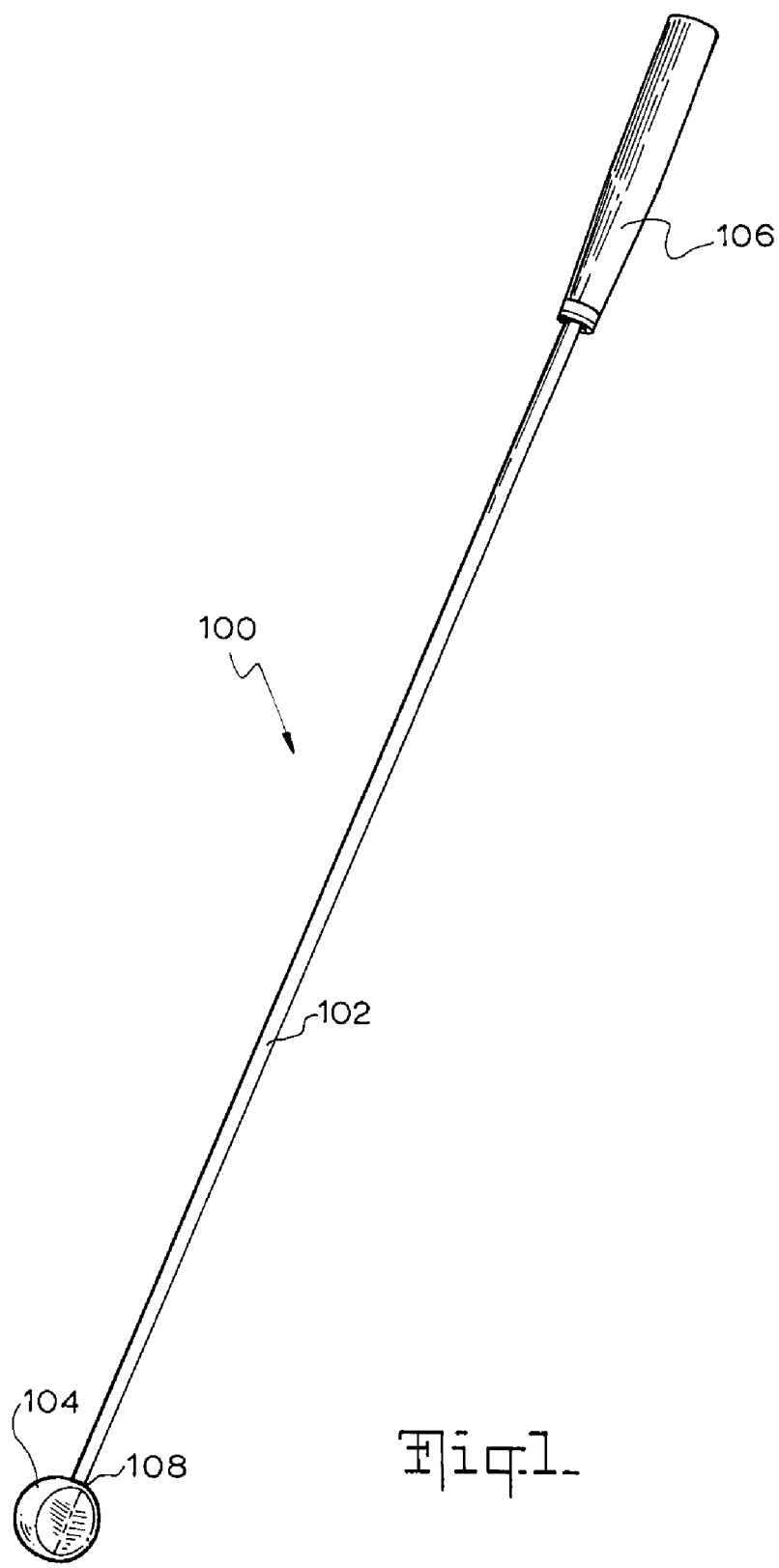
FIG. 1 is a perspective view of a pest inspection tool having a head and a shaft in accordance with a preferred embodiment of the present invention.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

Reference will now be made in detail to the present preferred embodiments of the invention, examples of which are illustrated in the accompanying drawings.

FIGS. 1 to 8 show a preferred embodiment of a pest timber damage inspection tool 100 having a shaft 102 and a head 104. In use, a user grips a proximal end 106 of shaft 102 and taps head 104 against a baseboard 10 to detect variances in sound that indicate the presence of damage to exposed timbers. In a room where a carpet is present, the user slides a flat side of head 104 against baseboard 10 while using an edge on head 104 to move the carpet away from the baseboard. The user may optionally slide a portion of head 104 in a concave profile of moldings of decorative timbers. The preferred elements of tool 100 and their interrelationship are described below. The present invention will be described for use with carpet, though it will be understood that the present invention may be used with a variety of floor coverings.

Figure 2:
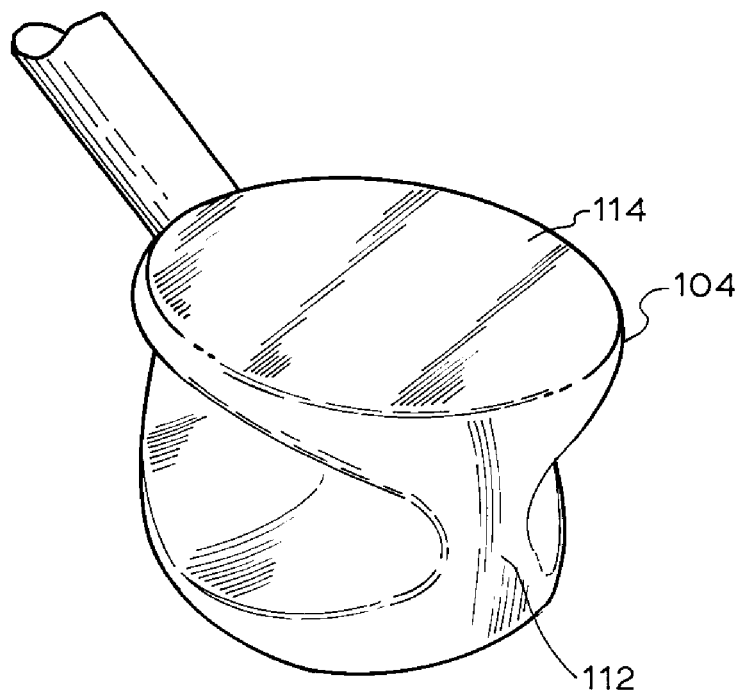
FIG. 2 is a rear perspective view of the head of the tool of FIG. 1.

Referring to FIGS. 1 and 2, tool 100 includes shaft 102 having proximal end 106, an opposite distal end 108, and a central longitudinal axis through ends 106, 108. Proximal end 106 is preferably configured for holding or gripping by the user and may be shaped in a variety of ways without departing from the scope of the present invention. Distal end 108 includes head 104 configured for engagement with a wall of a structure such as a house or commercial building.

As shown in FIGS. 2-7, head 104 has a top portion 110, a bottom portion 112, a rear portion 114, a front portion 116, a left side 118, and a right side 120. References to "left," "right" and "center" are for illustrative convenience only as would be appreciated by a person skilled in the art. Top and bottom portions 110, 112 are preferably arranged to intersect the central longitudinal axis of shaft 102 when head 104 is positioned at distal end 108 of shaft 102. Top portion 110 is preferably generally convex or dome-shaped and includes a pre-made aperture having a diameter sized for the insertion of shaft distal end 108 therein. Bottom portion 112 is preferably convex.

Figure 3:
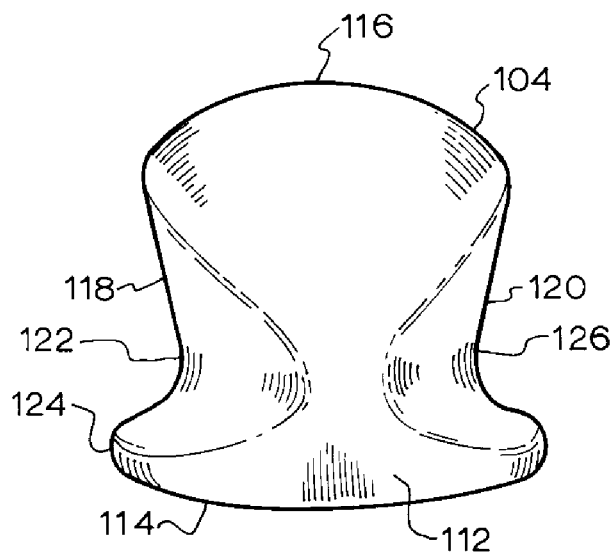
FIG. 3 is bottom elevation view of the head of FIG. 1 shown without a shaft.
Figure 4:
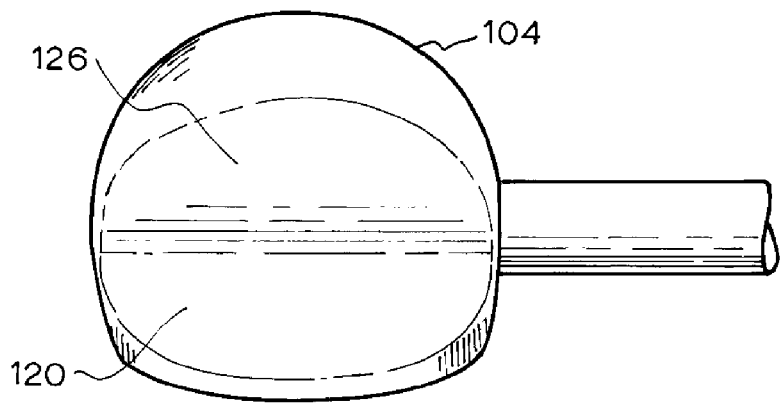
FIG. 4 is a right-side elevation view of the head of FIG. 1.

FIGS. 2-4 show rear portion 114 being substantially flat or planar along a rear plane parallel to the central longitudinal axis of shaft 102. Rear portion 114 is preferably configured to slide along a generally planar surface such as a wall. The generally planar surface of rear portion 114 provides stability to head 104 when tool 100 is used to check for pests along a lower portion of a wall adjacent a floor covering such as carpet.

Figure 5:
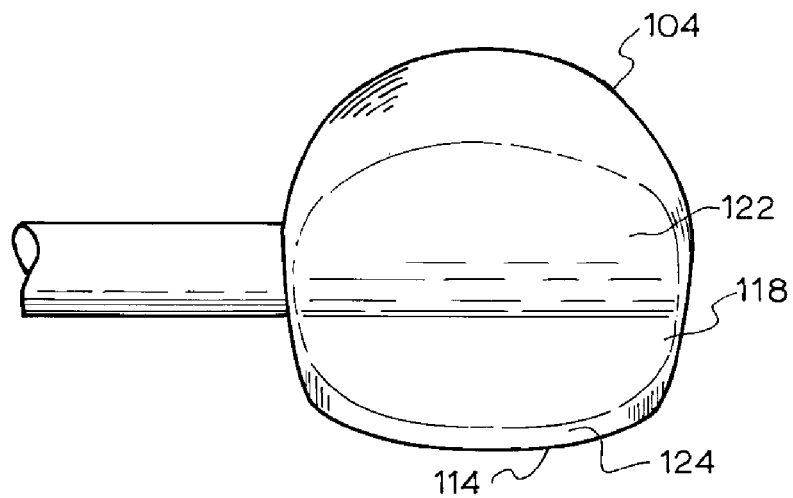
FIG. 5 is a left-side elevation view of the head of FIG. 1.
Figure 6:
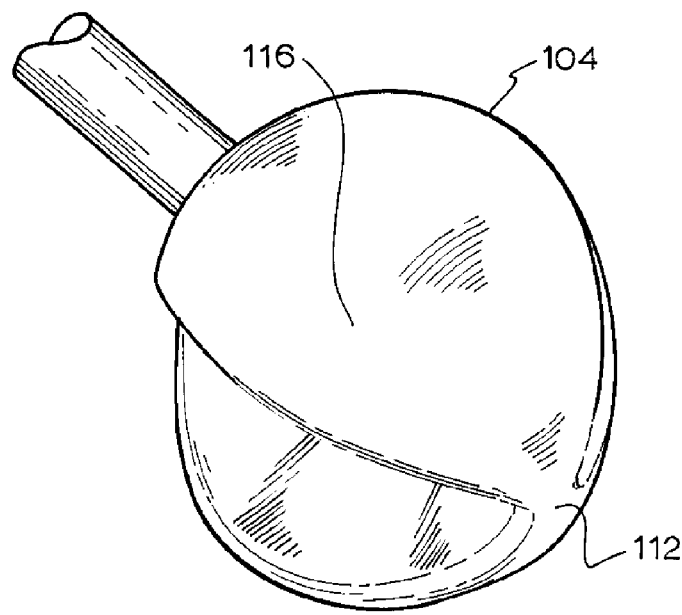
FIG. 6 is an expanded perspective view of the head of FIG. 1.

Head 104 includes a left side 118 as shown in FIG. 5. Left side 118 preferably includes a concave portion 122 that is concave in a plane perpendicular to the rear plane of rear portion 114, and perpendicular to the central longitudinal axis of shaft 102 when head 104 is engaged with shaft 102. Concave portion 122 preferably intersects with rear portion 114 to form an edge 124. As shown in FIGS. 3 and 5, edge 124 is preferably blunt-shaped, more preferably, slightly rounded. Edge 124 is configured to permit head 104 to penetrate into the boundary formed between the wall and the carpet over a substantial portion of the height of the carpet.

Referring to FIGS. 3 and 4, right side 120 is preferably opposite left side 118 and preferably identical in shape, including a concave portion 126. It will be appreciated that the concavity of concave portions 122 and 126 may be the same or different as desired.

Figure 7:
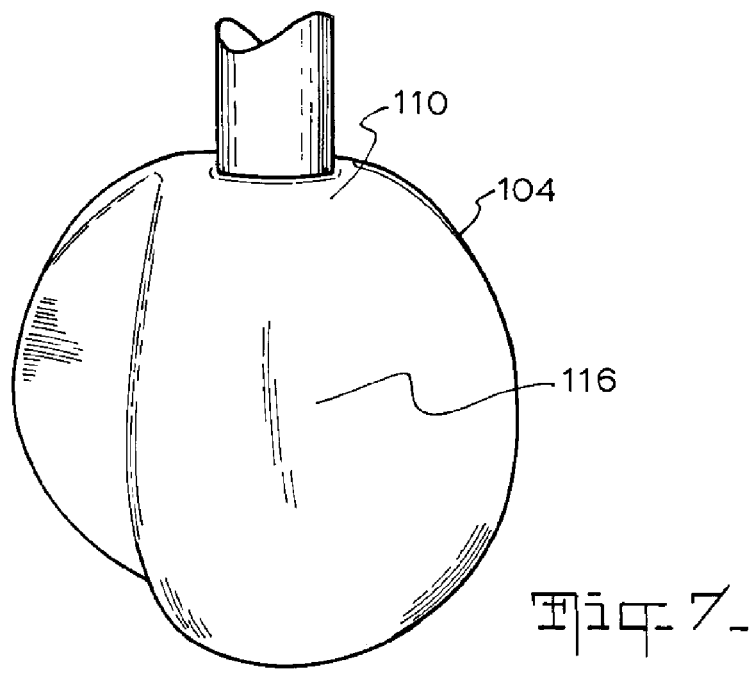
FIG. 7 is a front elevation view of the head of FIG. 1.

As shown in FIG. 7, front portion 116 is preferably convex. It will be appreciated that the front portion may be shaped differently as desired.

Shaft 102 and head 104 are preferably made of different materials. For example only, shaft 102 is preferably made of a metal, while head 104 is preferably made of a plastic or rubber material. It will be understood that a variety of materials may be used to construct tool 100 without departing from the scope of the present invention.

Head 104 is preferably attachable to shaft 102 by inserting distal end 108 of shaft 102 into the aperture in top portion 110 of head 104. Where desired, tool 100 may be formed as a unitary piece without detachable parts. The attachment of head 104 to shaft 102 may be made permanent if desired.

Figure 8:
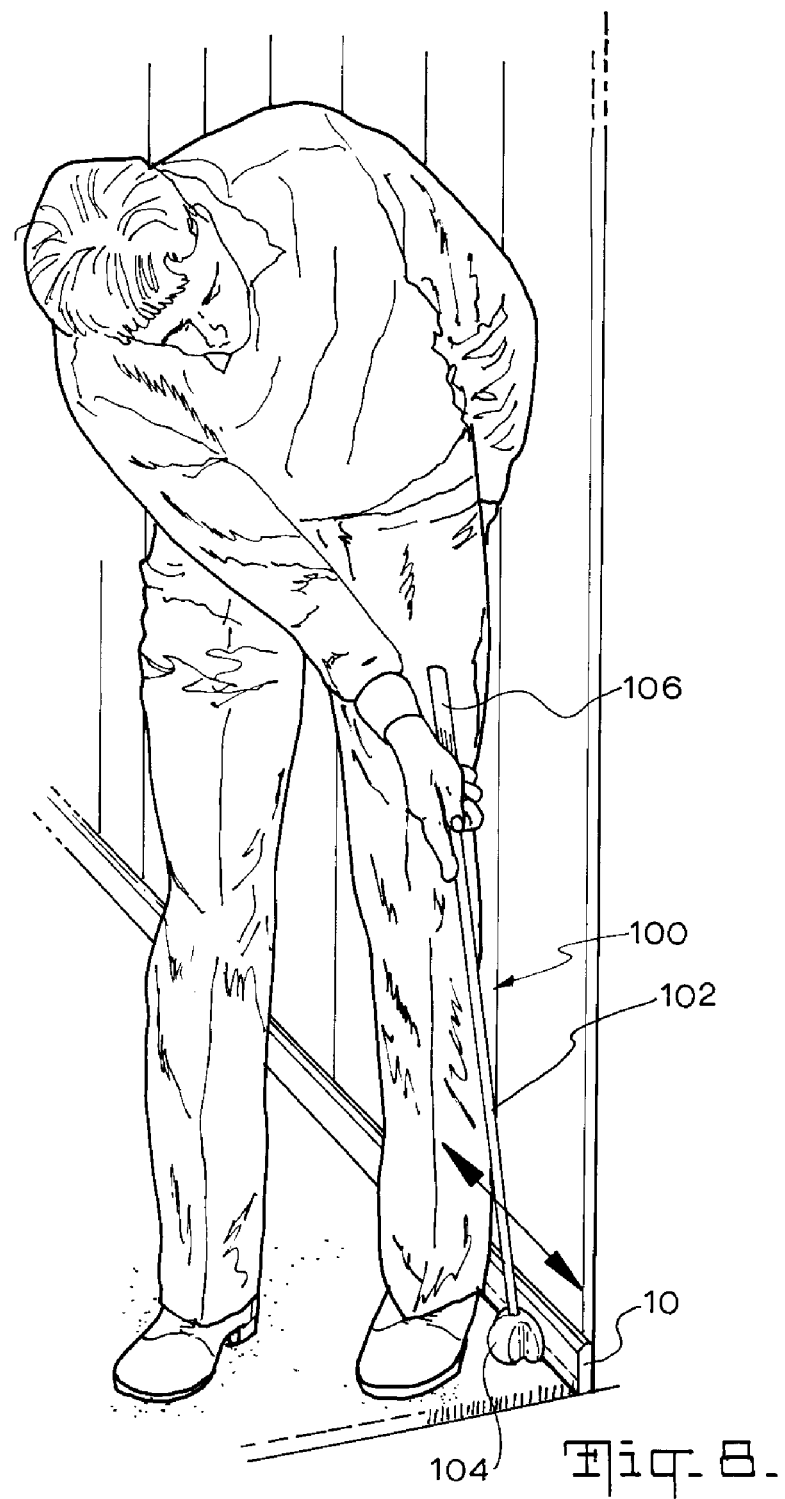
FIG. 8 is a perspective view of the tool of FIG. 1 in a preferred use.

Having described the preferred components of tool 100, a preferred method of use will now be described with reference to FIGS. 1 and 8. In use, a user grips proximal end 106 of shaft 102 and taps baseboard 10 of a wall with the convex front portion 116 of head 104. The user may alternatively or additionally tap or slide a portion (for example, the flat portion, convex portion, or concave portion) of head 104 into a deviation (where present) in a portion of a timber structure. For example only, edge 124 may be slid or tapped along a portion of a length of a longitudinal groove where the groove is a V-shaped notch or a concave molding. The shape of head 104 advantageously permits it to penetrate to a greater depth into the timber, which enhances the detection of any timber damage therein.

When in a room having a floor covering, such as carpet, the user engages the generally flat surface of rear portion 114 of head 104 against baseboard 10, lowering head 104 toward the floor and slides the head along the baseboard. While sliding head 104 along the baseboard, edge 124 moves the carpet away from the baseboard, permitting head 104 to penetrate to a greater depth towards the floor and enhancing the possible discovery of timber damage.

It will be appreciated that the steps described above may be performed in a different order, varied, or certain steps omitted entirely without departing from the scope of the present invention. For example, the user need not use front portion 116 to first tap a wall.

The foregoing description is by way of example only, and may be varied considerably without departing from the scope of the present invention. For example only, the curvature along the left and right sides of head 104 may be different relative to one another and have a different arc of radius. One side may be convex while another side concave. If desired, flat portions may be placed along any of the surfaces of head 104 to create a plurality of facets or scallops. The edge may be formed as a sharp edge. A portion of the shaft and/or head may be hollow. The depth of the aperture in the head may extend more than half the height of the head, or all the way through the head. The shaft may be fixed to the head using other means such as a concave plate with attachments means on an interior surface to engage the exterior surface of the top portion of the head.

The features described with respect to one embodiment may be applied to other embodiments, or combined with or interchanged with the features of other embodiments, as appropriate, without departing from the scope of the present invention.

The present invention in a preferred form provides the advantages of enhancing the opportunity to discover timber damage in interior environments that present challenges, such as a carpeted floor.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A tool for inspecting timber of a structure for the presence of damage to exposed timber caused by a pest, the tool comprising:
 a shaft having a proximal end, a distal end and a central longitudinal axis through said proximal and distal ends, said proximal end being configured to be gripped by a user; and
 a head at said distal end, said head including a top portion for engagement with said distal end of said shaft and a bottom portion opposite said top portion, said top and bottom portions intersecting the central longitudinal axis of said shaft when said head is engaged thereto, said head including a rear portion and a front portion opposite said rear portion, said rear and front portions each extending from said top portion to said bottom portion, said rear portion being substantially flat along a rear plane parallel to the central longitudinal axis of said shaft, said head including opposed sides, said opposed sides each extending from said rear portion to said front portion, said opposed sides each extending from said top portion to said bottom portion, at least one of said sides having a concave portion that is concave in a plane perpendicular to the rear plane and perpendicular to the central longitudinal axis of said shaft when said head is engaged with said shaft, said concave portion of said at least one of said sides forming an edge with said rear portion, said edge being configured to permit said head to penetrate into a surface deviation in the timber, or into a boundary between the timber and a floor covering over a substantial portion of the height of the floor covering.

2. The tool of claim 1, wherein said head is solid.

3. The tool of claim 1, wherein said head is detachable from said shaft.

4. The tool of claim 1, wherein said head comprises a plastic material.

5. The tool of claim 1, wherein both of said sides include a concave portion.

6. The tool of claim 5, wherein said concave portions have the same arc of radius.

7. The tool of claim 5, wherein said concave portions each have an arc of radius that are different relative to each other.

8. The tool of claim 1, wherein said head is formed with an aperture in said top portion, said shaft being insertable into said aperture.

9. The tool of claim 1, wherein said front portion is convex.

10. The tool of claim 1, wherein said top and bottom are convex.

11. The tool of claim 1, wherein said edge is blunt.

12. The tool of claim 1, wherein said edge is rounded.

13. The tool of claim 1, wherein said edge is sharp.

14. The tool of claim 1, wherein said shaft and said head are made of different materials.

15. The tool of claim 1, wherein said shaft is metallic.

* * * * *